United States Patent [19]

Zupancic et al.

[11] Patent Number: 4,928,292
[45] Date of Patent: May 22, 1990

[54] GANTRY TILT AND SUPPORT ASSEMBLY FOR CT SCANNER

[75] Inventors: Anton Z. Zupancic, Kirtland; Joseph S. Deucher, Lyndhurst, both of Ohio

[73] Assignee: Picker International, Inc., Highland Hts., Ohio

[21] Appl. No.: 276,243

[22] Filed: Nov. 25, 1988

[51] Int. Cl.⁵ ............................................. H05G 1/60
[52] U.S. Cl. ........................................... 378/17; 378/4
[58] Field of Search ..................................... 378/17, 4

[56] References Cited

U.S. PATENT DOCUMENTS

| | | |
|---|---|---|
| 4,088,888 | 5/1978 | Brook et al. . |
| 4,093,861 | 6/1978 | Kelman et al. . |
| 4,093,862 | 6/1978 | Brandt et al. . |
| 4,750,195 | 6/1988 | Takahashi ............................. 378/17 |
| 4,983,860 | 6/1978 | Kelman et al. . |

Primary Examiner—Craig E. Church
Attorney, Agent, or Firm—Fay, Sharpe, Beall, Fagan, Minnich & McKee

[57] ABSTRACT

A computerized tomographic scanning apparatus comprises a gantry assembly for performing tomographic examination and including a detector and data acquisition assembly carried on a first frame for selective rotation about a first axis. A base frame supports the first frame for limited tilting movement about a second axis which lies in a plane generally perpendicular to the first axis. A selectively operable drive assembly for tilting the gantry assembly about the first axis comprises first and second extensible and retractable rotary drive screw assemblies connected between the first frame and the second frame at locations spaced laterally outwardly on opposite sides of the first axis. Each drive screw assembly includes a first end connected to the base frame and a second end connected to the first frame at a point radially outwardly of the second axis. Electric motor and control units are provided for producing simultaneous operation of the first and second drive screw assemblies for producing controlled tilting movement of the first frame about the second axis. Also, the control units includes controls for deenergizing the electric motors if either of the drive screw assemblies fails to operate when its respective electric motor is energized.

10 Claims, 4 Drawing Sheets

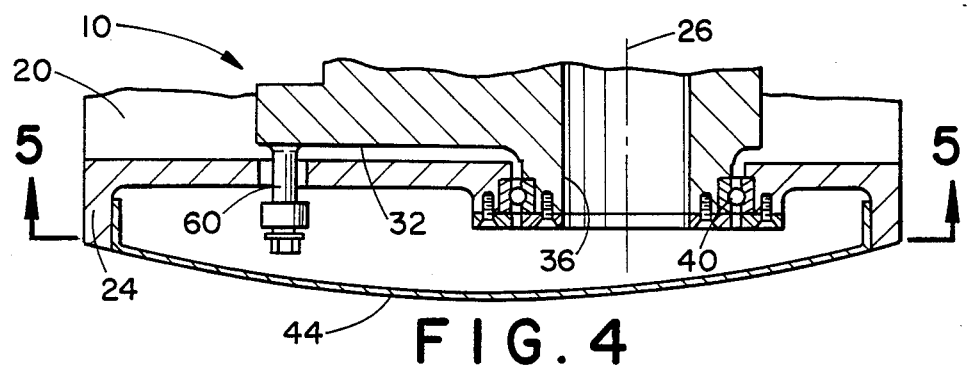
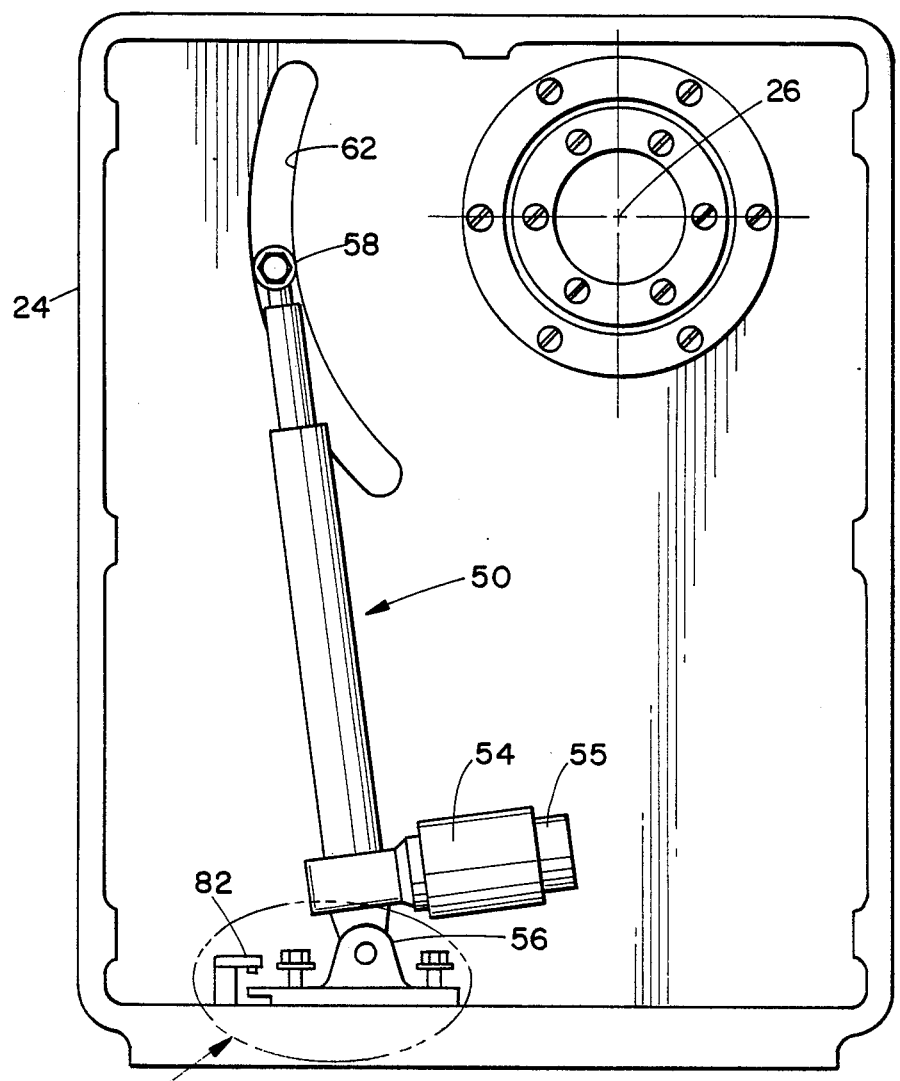

GANTRY TILT AND SUPPORT ASSEMBLY FOR CT SCANNER

BACKGROUND OF THE INVENTION

The present invention pertains to the art of medical diagnostic imaging and, more particularly, to a computerized tomographic (CT) scanner apparatus.

The typical CT scanner apparatus uses an X-ray source and a multiple array of X-ray detectors which are carried on opposite sides of a frame mounted for rotation about a longitudinal axis which is generally horizontally disposed. During rotation a longitudinally thin X-ray beam is projected through a subject or patient positioned on the longitudinal axis. The detectors develop signals indicative of X-ray transmission characteristics through the subject. The signals are suitably modified and/or amplified and used by a computer to control a cathode ray tube or the like for forming a reconstructed image of the layer through which the X-ray beam has passed.

Normally, the X-ray beam is projected through a thin layer of the subject's body so that the layer of the reconstructed image is perpendicular to the longitudinal axis on which the patient is disposed. In certain instances, however, the type of diagnostic information required can best be obtained by viewing a layer through the subject's body which is tilted slightly through a small vertical angle which is not perpendicular to the longitudinal axis along which the patient is positioned.

Different types of support frames and mechanisms have been proposed for providing the various rotational, translational and tilting functions discussed above. Generally, however, the prior support frames and mechanisms have been unduly complex and/or unable to satisfactorily perform the tilting function.

BRIEF DESCRIPTION OF THE INVENTION

The subject invention provides a gantry support assembly for a CT scanner which provides a relatively simple but highly effective arrangement for allowing the gantry to be selectively tilted.

In particular, according to the subject invention, a computerized tomographic scanner apparatus is provided with a base frame means that includes a pair of laterally spaced and generally vertically extending support members. A gantry assembly is carried by the support members by bearing means arranged to permit the gantry assembly to be tilted about a first generally horizontal axis extending between the vertically extending support members. Drive means are provided for selectively tilting the gantry assembly about the first axis. The drive means include a first longitudinally extensible and retractable power unit having a first end connected to the base frame and a second end connected to the gantry assembly at a point spaced radially outwardly of the first axis. Control means are also provided for controlling the extension and retraction of the power unit.

In accordance with a more limited aspect of the invention the drive means preferably include a second longitudinally extensible and retractable power unit having one end connected to the base frame means and a second end connected to the gantry assembly at a point spaced radially outwardly of the first axis. Preferably, the first and second power units are mounted in separate ones of the vertically extending support members. By controlling the actuation of the first and second power units the gantry assembly can be caused to selectively tilt about the first axis.

Preferably, and in accordance with a further more limited aspect of the invention, the first and second power units comprise separate ball type drive screws which are independently driven by separate electric motors. Preferably, the control means include means for assuring that the drive screws are driven in unison an equal amount per unit of time. In this regard, the control means preferably include Hall effect sensors for controlling the operation of the first and second electric drive motors to achieve equal speeds.

In addition to the above, the apparatus preferably includes means for deenergizing the electric motors if either of the drive screw assemblies fails to operate when its respective electric motor is energized. In this manner, a failure of one of the drive screws cannot result in damage to the gantry assembly by continued operation of the other motor end drive screw assembly.

As is apparent from the foregoing, a primary object of the present invention is the provision of a highly simplified and effective arrangement for producing selective tilting of a CT scanner gantry assembly.

A further object is the provision of an apparatus of the type describe wherein a pair of separately driven drive screw assemblies provide a positive tilting movement to a CT scanner gantry assembly.

Yet another object of the invention is the provision of an apparatus of the type described which includes interlock means for preventing operation of one of the drive screws when the other fails to operate properly.

An advantage of the present invention is that the tilting drive units can be totally enclosed in the vertical side frames to provide a highly compact and simplified structure.

Still other objects and advantages of the present will become apparent to those skilled in the art upon reading and understanding the following detailed description of the preferred embodiment.

BRIEF DESCRIPTION OF THE DRAWINGS

The present invention make take form in various parts and arrangement of parts, and various steps and arrangements of steps. The drawings are only for the purpose of illustrating preferred embodiments and are not to be construed as limiting the invention.

FIG. 4 is a cross-sectional view similar to FIG. 2 but showing the left hand vertical support element of the main gantry support base frame;

FIG. 5 is a cross-sectional view taken on line 5—5 of FIG. 4;

DETAILED DESCRIPTION OF THE PREFERRED EMBODIMENT

Figure 1:
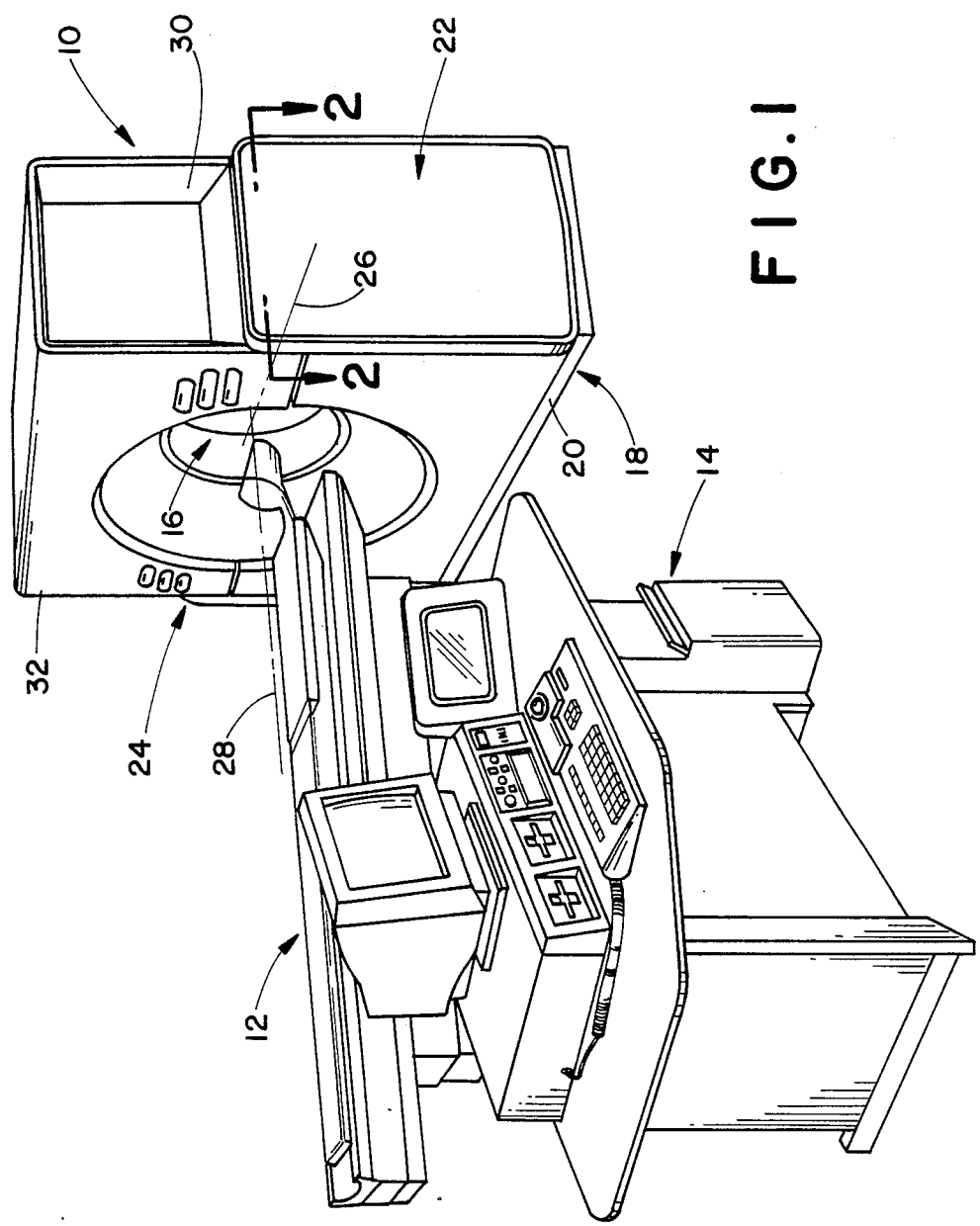
FIG. 1 is a pictorial showing, somewhat diagrammatic, of the overall arrangement of a CT scanner system incorporating the present invention.

With particular reference to FIG. 1 a CT scanner system is broadly illustrated as including a gantry unit 10, a stationary patient couch 12 and an operator console 14. In some installations and applications, the patient couch 12 is arranged to move or present the patient to the gantry assembly 10 in an incremented series of steps along a horizontal axis extending centrally through the gantry unit 10. In other embodiments, the couch moves continuously to move the patient through the center of the gantry unit 10 such that the patient is scanned along helical paths.

Within the gantry unit 10, a rotating anode X-ray tube or radiation source (not shown) is arranged to emit a fanned shaped beam of radiation toward and spanning the scan circle 16. Across the scan circle 16 from the X-ray tube is an array of detectors (not shown) which receive the X-ray beams and produce an output indicative of the tissue density through which the beam has passed. The signals produced by the detectors are conveyed to the console 14 and computer processed in a well known manner to produce a reconstructed image which may be stored in the console or displayed on one or more video monitors.

As previously discussed, the X-ray tube and detectors are typically rotated about the scan circle in a plane perpendicular to the longitudinal axis 28 on which the patient or subject is presented to the gantry. In certain instances, it is desirable to tilt the scan circle 16 slightly with respect to the normally horizontal longitudinal axis. For this reason, the subject invention mounts the gantry 10 in a main base frame assembly 18 which includes a generally horizontally extending rigid base member 20 and a pair of laterally spaced and vertically extending rigid support column members 22 and 24. The support column members 22 and 24 are rigidly connected to the main base member 20 and support the gantry unit 10 for tilting movement about an axis 26 which is perpendicular to the patient presentation axis identified as 28. In addition, the axis 26 preferably intersects the axis 28. Also, it should be noted that in the subject embodiment, both the axes 26 and 28 are preferably horizontal although, it is readily apparent that these axes could be tilted.

Figure 2:
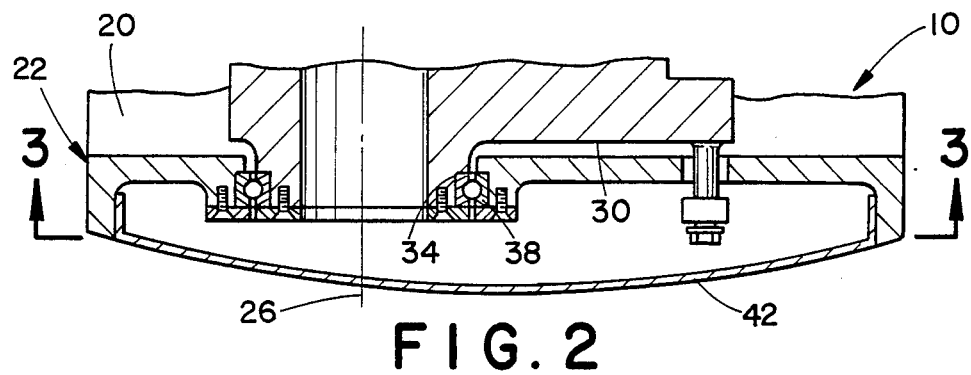
FIG. 2 is a cross-sectional view taken on line 2—2 of FIG. 1 and showing the right hand vertical support section of the main gantry support frame.

In order to provide the pivotal movement required, the gantry assembly 10 is provided on its right and left lateral side ends 30 and 32 with outwardly extending cylindrical trunnion members 34 and 36 respectively. As illustrated in FIGS. 2 and 4, the trunnions 34 and 36 are suitably supported by ball bearing assemblies 38 and 40 respectively. The bearing assemblies 38 and 40 are respectively mounted and retained in the vertically extending right and left support column members 22 and 24 in a conventional manner.

In the subject embodiment, the support column members 22 and 24 extend vertically upward from the base member 20 and include outer sheet metal cover plate members 42 and 44 which define enclosed chambers in the support columns.

Figure 3:
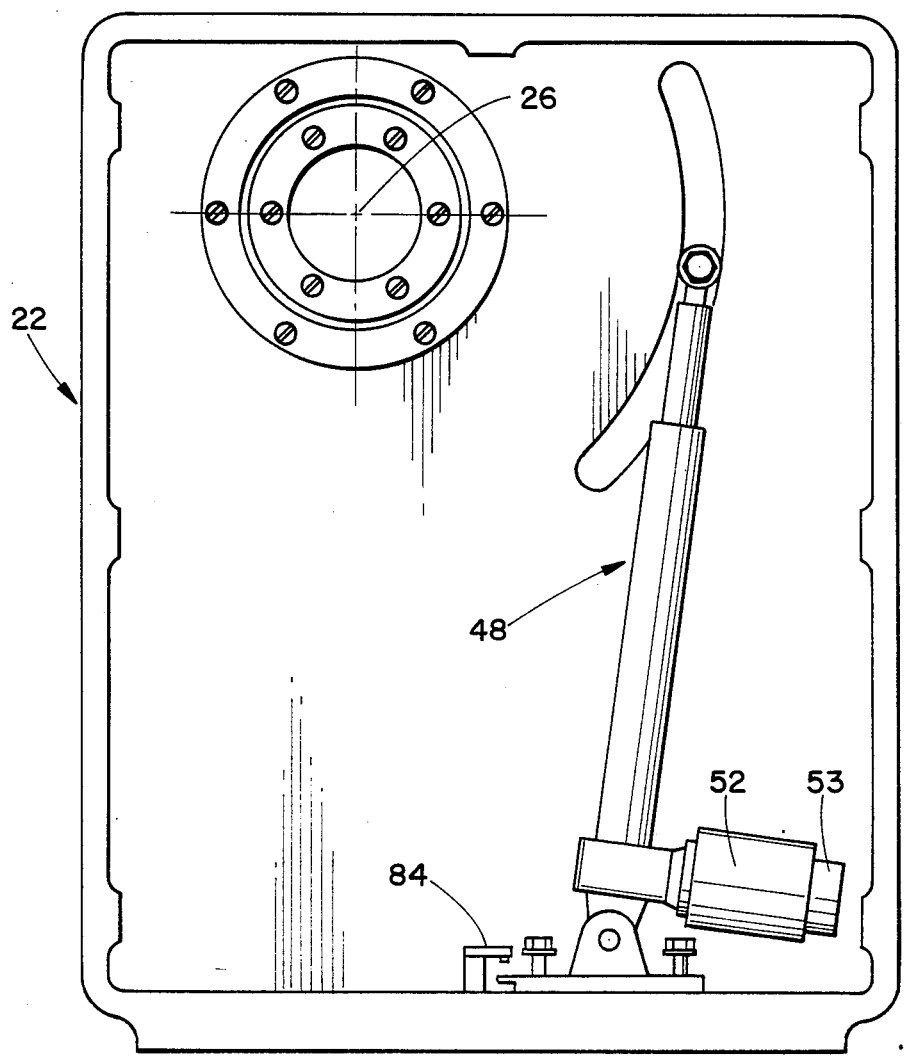
FIG. 3 is cross-sectional view taken along line 3—3 of FIG. 2.

The gantry assembly 10 is selectively driven for tilting movement about axis 26 by first and second longitudinally extensible and retractable power units 48 and 50 (see FIGS. 3 and 5) which are respectively carried in the enclosed chambers of the right and left vertical support column members 22 and 24 respectively. In the subject embodiment, the power units 48 and 50 are conventional ball screw actuators which are each separately driven by independent DC electric motors 52 and 54 respectively. In general, each of the actuators is mounted in the same manner and accordingly, only actuator 50 will be described in detail. More particularly, referring to FIG. 5, the lower end of actuator 50 is connected through a pivot pin with a mounting bracket 56 that is suitably bolted or otherwise connected to the bottom of the left support column 24 in a manner to be subsequently described. The upper or output end of the actuator 50 is pivotally connected at 58 to a pin member 60 which extends from the end 32 of the gantry assembly 12. Pin 60 is suitably located a radial distance outwardly of axis 26 and extends through an arcuate opening 62 formed through the support column 24. Actuator 48 is connected in operational relationship to the gantry unit by a duplicate arrangement as illustrated in FIG. 3. As can be appreciated, during extension and retraction of the power units 48 and 50 the gantry assembly 10 is caused to be tilted about the axis 26.

Figure 7:
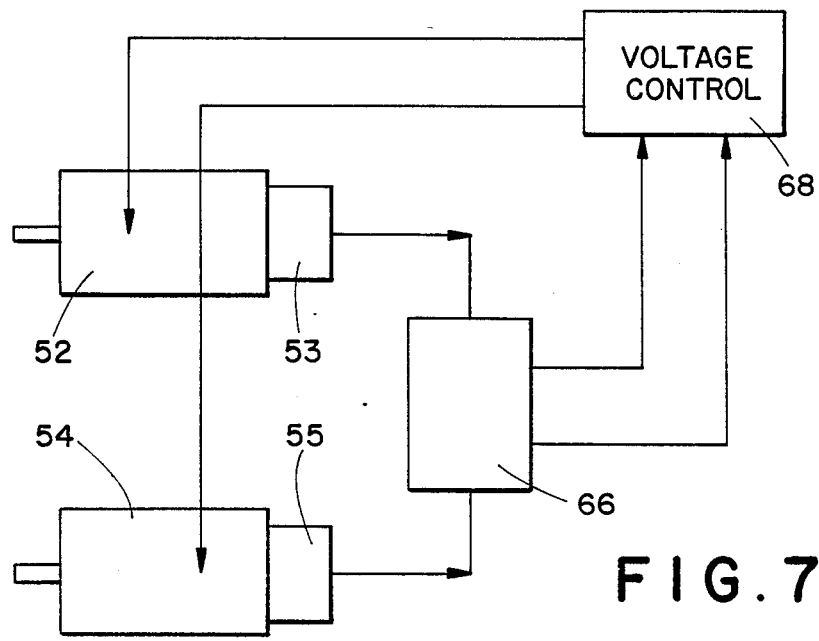
FIG. 7 is a diagrammatical representation of the motor control circuitry.

The DC drive motors 52 and 54 are controlled to operate simultaneously at substantially the same rate of speed so that movement of the two power units 48, 50 is equal and simultaneous. In this regard, each of the motors 52, 54 is provided with a separate respective Hall effect sensor unit 53, 55. The output from the individual Hall sensor units is indicative of the speed of the associated DC motor 52 or 54, respectively. As illustrated diagrammatically in FIG. 7, the output from the two Hall sensor units is conducted to a comparator 66. If the difference between the two signals exceeds a predetermined level, signals to a voltage control unit 68 result in a change in the voltage supplied to the DC motors 52 or 54 to cause the motors to achieve the same output as measured by their respective Hall sensor units. This arrangement thus assures that each of the motors are performing an equal portion of the tilting function.

Figure 6:
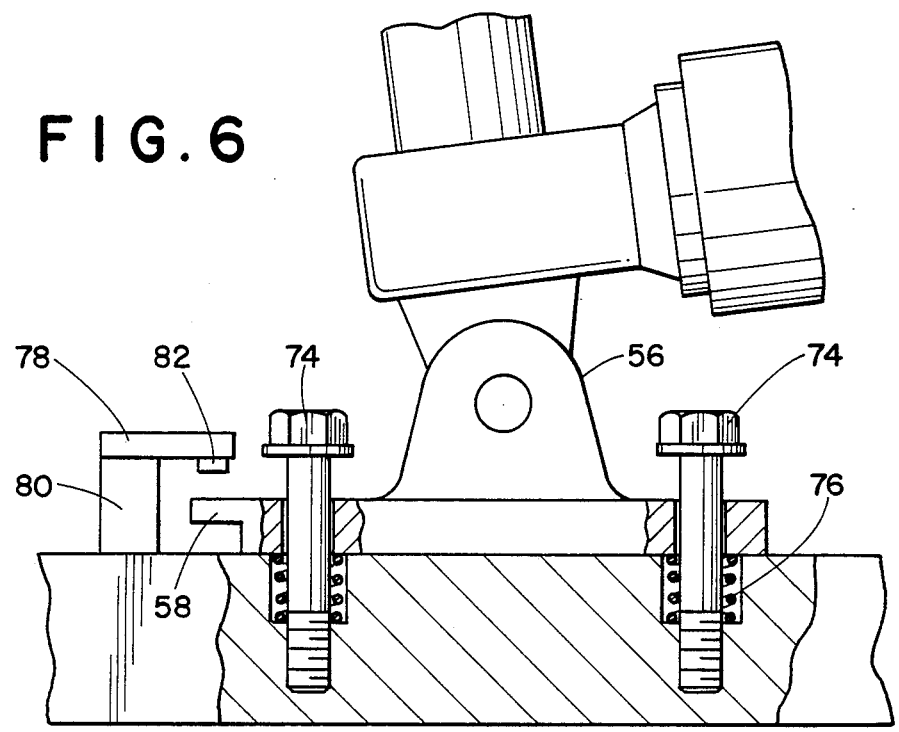
FIG. 6 is an enlarged view of the circled area of FIG. 5.

The subject invention further includes means for preventing damage to the gantry or the power units if for any reason one of the power units fails to operate properly. In this regard, each of the power units is provided with means which can discontinue flow of power to the power units if either is stopped while the other is operating. In particular, referring to FIGS. 5 and 6, it will be noted that mounting bracket 56 is joined to the bottom of the support column member 24 by a pair of bolts or studs 74 which pass through suitable openings in the base of the bracket 56 and into threaded openings in the bottom of the column 24. Springs are positioned in recesses on the support column member 24 such that the springs bear against the underside of mounting bracket 56. Many different types of springs and spring arrangements could be used but, in the subject embodiment, the springs are illustrated as a pair of helical compression springs 76. Spring length and spring rate are selected such that the static downward acting force exerted by power unit 54 compresses springs 76 and holds mounting bracket 56 against the bottom of column 24. A similar arrangement is used for mounting the support bracket for power unit 48.

Extending outwardly from the end of the bracket 56 is a rigid finger member 58. A switch member 78 is mounted on a suitable bracket or support 80 such that its operator 82 is located immediately above the finger 58. As shown in FIG. 5, a duplicate switch and operator arrangement is carried on the support or mounting bracket of unit 48. The switch for the unit 48 is generally indicated with the reference numeral 84.

The switches 78 and 84 are connected through conventional circuitry, not shown, such that if either is moved to an off position through contact with the associated operating finger, power to the motors 52, 54 is discontinued. In particular, to understand the operation of the switches 58 assume that the power unit 48 fails while the power unit 50 is moving upwardly. As power unit 58 moves upwardly it causes the gantry unit 10 to be moved in a clockwise direction about axis 26 as viewed in FIG. 5. This produces pulling or upward movement on the stopped power unit 48 (see FIG. 3). Upward movement of course, causes its operating finger to contact the switch 84 moving it to a closed position. Conversely, if we assume that unit 48 fails while the power unit 50 is in the process of lowering the gantry or moving in a counterclockwise direction about axis 26 as viewed in FIG. 5 then the power unit 48 acts as a rigid rod and continued actuation of power unit 50 causes it to pull upwardly. This causes the finger 58 to move into contact with the switch 82 moving it to a position therein power to the two DC motors 52, 54 is discontinued. Another failure mode of power unit 50 would result in its inability to support the gantry load imposed on it at 58 by pin member 60. This failure would cause compressed springs 76 to move mounting bracket 56 upwards and result in finger 58 moving into contact with switch 82 and discontinue power to power units 48 and 50. In this manner, the failsafe operation of the gantry tilting drive is assured.

The invention has been described in great detail sufficient to enable one of ordinary skill in the art to make and use the same. Obviously, alterations and modifications will occur to others upon a reading and understanding of the specification and it is our intention to include all such modifications and alterations as part of our invention insofar as they come within the scope of the appended claims.

Having thus described the preferred embodiment, the invention is now claimed to be:

1. Computerized tomographic scanner apparatus comprising:
   a base frame means including a pair of laterally and vertically extending support members;
   a gantry assembly including a source of penetrating radiation and a detector for detecting radiation coming from said source; said gantry assembly carried by said support members by bearing means arranged to permit said gantry assembly to be tilted about a first generally horizontal axis extending between said vertically extending support members;
   drive means for selectively tilting said gantry assembly about said first axis, said drive means including first and second longitudinally extensible and retractable power units each including a separate respective motor associated therewith and having a first end connected to said base frame and a second end connected to said gantry assembly at a point spaced radially outward of said first axis;
   control means for controlling the operation of said power units including means for producing synchronous movement of said power units; and,
   said control means further including means responsive to failure of operation of either of said power units for stopping the motor associated with the other power unit.

2. The apparatus of claim 1 wherein said first and second power units are mounted in separate ones of said vertically extending support members.

3. Computerized tomographic scanner apparatus comprising:
   a base frame means including a pair of laterally and vertically extending support members;
   a gantry assembly including a source of penetrating radiation and a detector for detecting radiation coming from said source; said gantry assembly carried by said support members by bearing means arranged to permit said gantry assembly to be tilted about a first generally horizontal axis extending between said vertically extending support members;
   drive means for selectively tilting said gantry assembly about said first axis, said drive means including a first longitudinally extensible and retractable power unit having a first end connected to said base frame and a second end connected to said gantry assembly at a point spaced radially outward of said first axis;
   control means for controlling the extension and retraction of said power unit;
   said drive means further including a second longitudinally extensible and retractable power unit having one end connected to said base frame means and a second end connected to said gantry assembly at a point spaced radially outwardly of said first axis, said first and second power units being independently actuated by separate first and second electric drive motors; and,
   said control means including means responsive to failure of either of said electric motors for deenergizing the other of said electric motors.

4. The apparatus of claim 3 wherein said first and second power units comprise separate drive screws.

5. The apparatus of claim 4 wherein said separate drive screws are independently driven by separate electric motors and wherein said control means include means for producing output signals indicative of the number of revolutions made by said electric motors.

6. Computerized tomographic scanner apparatus comprising:
   a base frame means including a pair of laterally and vertically extending support members;
   a gantry assembly including a source of penetrating radiation and a detector for detecting radiation coming from said source; said gantry assembly carried by said support members by bearing means arranged to permit said gantry assembly to be tilted about a first generally horizontal axis extending between said vertically extending support members;
   drive means for selectively tilting said gantry assembly about said first axis, said drive means including a first longitudinally extensible and retractable power unit having a first end connected to said base frame and a second end connected to said gantry assembly at a point spaced radially outward of said first axis;
   control means for controlling the extension and retraction of said power unit;
   said drive means further including a second longitudinally extensible and retractable power unit having one end connected to said base frame means and a second end connected to said gantry assembly at a point spaced radially outwardly of said first axis, said first and second power units being independently actuated by separate first and second electric drive motors; and, Hall effect sensors for controlling the operation of said first and second electric drive motors.

7. Computerized tomographic scanner apparatus comprising:
 a base frame means including a pair of laterally and vertically extending support members;
 a gantry assembly including a source of penetrating radiation and a detector for detecting radiation coming from said source; said gantry assembly carried by said support members by bearing means arranged to permit said gantry assembly to be tilted about a first generally horizontal axis extending between said vertically extending support members;
 drive means for selectively tilting said gantry assembly about said first axis, said drive means including a first longitudinally extensible and retractable power unit having a first end connected to said base frame and a second end connected to said gantry assembly at a point spaced radially outward of said first axis;
 control means for controlling the extension and retraction of said power unit;
 said drive means further including a second longitudinally extensible and retractable power unit having one end connected to said base frame means and a second end connected to said gantry assembly at a point spaced radially outwardly of said first axis, said first and second power units being independently actuated by separate first and second electric drive motors; and
 sensing and control means for preventing operation of both said drive motors if either of said power units fails to operate.

8. Computerized tomographic scanner apparatus comprising:
 a gantry assembly for performing tomographic examination and including a source of penetrating radiation and a detector for detecting radiation coming from said source, said gantry assembly carried on a first frame for selective rotation about a first axis;
 a base frame for supporting said first frame for limited tilting movement about a second axis which lies in a plane generally perpendicular to said first axis;
 selectively operable drive means for tilting said gantry assembly about said second axis, said drive means including first and second extensible and retractable rotary drive screw assemblies connected between said first frame and said second frame at locations spaced laterally outwardly on opposite sides of said first axis, each said drive screw assembly having a first end connected to said base frame and a second end connected to said first frame at a point radially outwardly of said second axis;
 power and control means for producing simultaneous operation of said first and second drive screw assemblies for producing controlled tilting movement of said first frame about said second axis;
 said power and control means including a separate electric motor for each of said first and second drive screw assemblies; and,
 wherein said power and control means include means for deenergizing said electric motors if either of said drive screw assemblies fails to operate when its respective electric motor is energized.

9. Computerized tomographic scanner apparatus comprising:
 a gantry assembly for performing tomographic examination and including a source of penetrating radiation and a detector for detecting radiation coming from said source, said gantry assembly carried on a first frame for selective rotation about a first axis;
 a base frame for supporting said first frame for limited tilting movement about a second axis which lies in a plane generally perpendicular to said first axis;
 selectively operable drive means for tilting said gantry assembly about said second axis, said drive means including first and second extensible and retractable rotary drive screw assemblies connected between said first frame and said second frame at locations spaced laterally outwardly on opposite sides of said first axis, each said drive screw assembly having a first end connected to said base frame and a second end connected to said first frame at a point radially outwardly of said second axis;
 power and control means for producing simultaneous operation of said first and second drive screw assemblies for producing controlled tilting movement of said first frame about said second axis;
 said power and control means including a separate electric motor for each of said first and second drive screw assemblies; and,
 wherein said power and control means includes Hall effect sensors for controlling operation of said electric motors to produce simultaneous and equal movement of said drive screw assemblies.

10. The apparatus as defined in claim 9 wherein said drive screw assemblies extend in parallel.

* * * * *